(12) United States Patent
Ghayur

(10) Patent No.: US 7,795,494 B2
(45) Date of Patent: Sep. 14, 2010

(54) TRANSGENIC MICE EXPRESSING ANTIBODIES SPECIFIC FOR GENES OF INTEREST AND USES THEREOF

(75) Inventor: Tariq Ghayur, Holliston, MA (US)

(73) Assignee: Abbott Laboratories, Abbott Park, IL (US)

( * ) Notice: Subject to any disclaimer, the term of this patent is extended or adjusted under 35 U.S.C. 154(b) by 166 days.

(21) Appl. No.: 10/104,148

(22) Filed: Mar. 22, 2002

(65) Prior Publication Data

US 2002/0138857 A1    Sep. 26, 2002

Related U.S. Application Data

(60) Provisional application No. 60/278,515, filed on Mar. 22, 2001.

(51) Int. Cl.
*A01K 67/027* (2006.01)
*C12N 15/00* (2006.01)

(52) U.S. Cl. .............................. 800/18; 800/21; 800/22

(58) Field of Classification Search .................... 800/8, 800/18, 21, 22, 25; 435/325, 326, 327, 331, 435/336
See application file for complete search history.

(56) References Cited

U.S. PATENT DOCUMENTS

| | | | |
|---|---|---|---|
| 4,736,866 A | 4/1988 | Leder et al. | 800/10 |
| 4,870,009 A | 9/1989 | Evans et al. | 435/69.4 |
| 4,873,316 A | 10/1989 | Meade et al. | 800/7 |
| 5,166,320 A | 11/1992 | Wu et al. | 530/395 |
| 5,223,409 A | 6/1993 | Ladner et al. | 435/69.7 |
| 5,897,861 A | 4/1999 | Fanger et al. | 424/136.1 |
| 5,939,598 A | 8/1999 | Kucherlapati et al. | 800/25 |
| 6,071,517 A | 6/2000 | Fanger et al. | 424/136.1 |
| 6,096,311 A | 8/2000 | Fanger et al. | 424/136.1 |

FOREIGN PATENT DOCUMENTS

| | | |
|---|---|---|
| EP | 0264166 | 8/1996 |
| WO | 90/11354 | 10/1990 |
| WO | 91/01140 | 2/1991 |
| WO | 91/19796 | 12/1991 |
| WO | 92/01047 | 1/1992 |
| WO | 92/09690 | 6/1992 |
| WO | 92/15679 | 9/1992 |
| WO | 92/18619 | 10/1992 |
| WO | 92/20791 | 11/1992 |
| WO | 92/20808 | 11/1992 |
| WO | 93/01288 | 1/1993 |
| WO | 93/04169 | 3/1993 |
| WO | 93/16177 | 8/1993 |
| WO | 93/22443 | 11/1993 |
| WO | WO 9514780 A2 * | 6/1995 |
| WO | 96/33735 | 10/1996 |
| WO | 96/34096 | 10/1996 |
| WO | 91/01140 | 2/1997 |
| WO | 97/29131 | 8/1997 |
| WO | WO 9729131 A1 * | 8/1997 |
| WO | 98/24893 | 6/1998 |
| WO | 99/53049 | 10/1999 |

OTHER PUBLICATIONS

Ge et al. Genbank Accession No. Z48768, Sep. 11, 1995.*
Akolkar et al. Genbank Accession No. AJ223535, Dec. 2, 1998.*
deWildt et al. JMB, 285: 895-901 (1999).*
Lonberg et al. Nature, 386:856-859 (1994).*
Holmes et al. Hybridoma, 19(5):363-367 (2000).*
Samstein Phil. Trans. R. Soc. Lond., 356: 749-758, 2001.*
Encyclopædia Britannica. Genetics, human. (2008). In Encyclopædia Britannica. Retrieved Aug. 31, 2008, from Encyclopædia Britannica Online: http://www.search.eb.com/eb/article-50734, pp. 1-13.*
Green, Larry T., "Antibody engineering via genetic engineering of the mouse: Xenomouse strains are a vehicle for the facile generation of therapeutic human monoclonal antibodies" Journal of Immunological Methods, vol. 231, pp. 11-23 (1999).
Roes, Jurgen et al., "Mouse anti-mouse IgD monoclonal antibodies generated in IgD-deficient mice" Journal of Immunological Methods, vol. 183, pp. 231-237 (1995).
Rossi, Fabio et al., "Recent advances in inducible gene expression systems" Current Opinion in Biotechnology, vol. 9, pp. 451-456 (1998).
Soriano, P et al., "Promoter Interaction in Retro virus Vectors Introduced into Fibroblasts and Embryonic Stem Cells", Journal of Virology, vol. 65:5, pp. 2314-2319 (1991).
Friedrich Glenn et al., "Promoter Traps In Embronic Stem Cells: A Genetic Screen to Identify and Mutate Developmental Genes in Mice", Genes & Development, vol. 5, pp. 1513-1523 (1991).

(Continued)

*Primary Examiner*—Thaian N Ton
(74) *Attorney, Agent, or Firm*—Diana M. Steel; Kenneth P. Zwicker

(57) ABSTRACT

The invention provides compositions and methods for the generation of novel non-human transgenic animals which contain an alteration in a gene of interest. These transgenic animals are capable of generating antibodies, e.g., human monoclonal antibodies, specific for the product of a gene of interest that has been functionally disrupted in the transgenic animal. Furthermore, the methods and compositions of the invention are suitable for use in the treatment, diagnosis, and imaging of disease.

10 Claims, No Drawings

OTHER PUBLICATIONS

Von Melchner, Harald et al., Selective Disruption of genes Expressed in Totipotent Embyonal Stem Cells, Genes & Developemnt, vol. 6, pp. 919-927(1992).

Hagen, F.S. et al., "Assaying the Quality of cDNA Libraries", BioTechniques, vol. 6:4, pp. 340-345 (1988).

Hoogenboom, Hennie et al., Multi-Subunit Proteins On The Surface of Filamentous Phage: Methodologies For Displaying Antibody (Fab) Heavy and Light Chains, Nucleic Acids Research. vol. 19:15, pp. 4122-4137 (1991).

Barbas, Carlos, et al., "Assembly of Combinatorial Antibody Libraries on Phage Surfaces: The Gene III Site", Proc. Natl. Acad. Sci., vol. 88, pp. 7978-7982 (1991).

Liang, Peng et al. "Differential Display Using One-Base Anchored Oligo-dT Primers", Nucleci Acids Research, vol. 22:25, pp. 5763-5764 (1994).

Hay, Beverly et al., "Bacteriaophage Cloning and *Escherichia coli* Expression of a Human IgM Fab", Human Antibody Hybridomas, vol. 3, pp. 81-85 (1992).

Huse, William et al., "Genereation of a Large Combinatorial Library of the Immunoglobulin Repertoire in Phage Lambda", Research Article, Dec., pp. 1275-1281 (1989).

McCafferty, John et al., "Phage Antibodies: Filamentous Phage Displaying Antibody Variable Domains", Nature, vol. 348, pp. 552-554 (1990).

Griffiths, Andrew et al., "Human Anti-Self Antibodies With High Specificity From Phage Display Libraries", The EMBO Journal, vol. 12:2, pp. 725-734 (1993).

Clackson, Tim et al., "Making Antibody Fragments Using Phage Display Libraries", Nature, vol. 352, pp. 624-628 (1991).

Hawkins, Robert E et al., "Selection of Phage Antibodies by Binding Affinity Mimicking Affinity Maturation", Journal of Molecular Biology, vol. 226, pp. 889-896 (1992).

Gram, Hermann et al., "In Vitro Selection and Affinity Maturation of Antibodies From a Naïve Combinatorial Immunoglobulin Library", Proc. Natl. Acad. Sci., vol. 89, pp. 3576-3580 (1992).

Fuchs, Patrick et al., "Targeting Recombinant Antibodies to the Surface of *Escheriachia coli*: Fusion to a Peptidoglycan Associated lipoprotein", Biotechnology, vol. 9 1369-1372 (1991).

Johnsson, Bo et al., "Immobilization of Protiens to a Carboxymethyldextran_Modified Gold Surface for Biospcific Interaction Analysis in Surface Plasmon Resonance Sensors", Analytical Biochemstry, vol. 198, pp. 268-277 (1991).

Garrard, Lisa J et al., "FAB Assembly and Enrichment in a Monovalent Phage Display System", Biotechnology, vol. 9, pp. 1373-1377 (1991).

Taylor, Lisa D. et al., "A Transgenic Mouse that Expresses a Diversity of Human Sequence Heavy and Light Chain Immunoglobulins", Nuceic Acids Research, vol. 20:23, pp. 6287-6295 (1992).

Kipriyanov Sergey M et al. "Single-Chain Antibody Streptavidin Fusions: Tetrameric Bifunctional scFv-Complexes with Biotin Binding Activity and Enhanced Affinity to Antigen", Hum Antibod Hybridomas, vol. 6:3, pp. 93-101 (1995).

Holliger, Philipp et al., ""Diabodies": Small bivalent and Bispecific Antibody Fragments", Proc Natl Acad Sci, vol. 90, pp. 6444-6448 (1993).

Bird, Robert E et al., "Sigle-Chain Antigen-Binding Proteins", Science Reports, vol. 242, pp. 423-242 (1988).

Cheng, Liang et al., "In Vivo Promoter Activity and Transgene Expression in Mammalian Somatic Tissues Evaluated by Using Particle Bombardment", Proc Natl Acad Sci, vol. 90, pp. 4455-4459 (1993).

Wolff Jon A et al., "Direct Gene Transfer into Mouse Muscle in Vivo", Science Reports, vol. 1465-1468 (1990).

Wilson, James M et al., "Hepatocyte-directed Gene Transfer in Vivo Leads to transient Improvement of Hypercholesterolemia in Low Density Lipoprotein Receptor-Deficient Rabbits", The Journal of Biological Chemistry, vol. 267, pp. 963-967 (1992).

Herz, Joachim et al., "Adenovirus-Mediated Transfer of Low Density Lipoprotein Receptor Gene Acutely Accelerates Cholesterol Clearance in Normal Mice", Proc Natl Acad Sci, vol. 90, pp. 2812-2816 (1993).

Rosenfeld Melissa A et al., "In Vivo Transfer of the Human Cystic Fibrosis Transmembrane Conductance Regulator Gene to the Airway Epithelium" Cell, vol. 68, 143-155 (1992).

Ferry, Nicholas et al., "Retroviral-Mediated Gene Transfer into Hepatocytes in Vivo", Proc Natl Acad Sci, vol. 88, pp. 8377-8381(1991).

Gossen, Manfred et al., "Tight Control of Gene Expression in Mammalian Cells by Tetracycline-Responsive Promoters", Proc Natl Acad Sci, vol. 89, pp. 5547-5551 (1992).

Kessel, Michael et al., "Murine Developmental Control Genes", Science Articles, vol. 249, pp. 249-379 (1990).

Byrne, GW, et al., "Multiplex Gene Regulation: A Two-Tiered Approach to Transgene Regulation in Transgenic Mice", Proc Natl Acad Sci, vol. 86, pp. 5473-5477 (1989).

Winoto, Astar et al., "A Novel, Inducible and T Cell-Specific Enhancer Located at the 3' End of the T Cell Receptor ? Locus", The EMBO Journal, vol. 8:3, pp. 729-733 (1989).

Hasty, P et al., "Introduction of a Subtle Mutation into the Hox-2.6 Locus in Embryonic Stem Cells", Nature, vol. 350, pp. 243-246 (1991).

Zhang, Hongbing et al., "Targeting Frequency for Deletion Vectors in Embryonic Stem Cells", Molecular and Cellular Biology, vol. 14:4, pp. 2404-210(1994).

Valancius, Vicky et al., "Testing an "In-Out" Targeting Procedure for Making Subtle Genomic Modifications in Mouse Embryonic Stem Cells", Molecular and Cellular Biology, vol. 11:3, pp. 1402-1408 (1991).

Wilmut, I et al., "Viable Offspring Derived from Fetal and Adult Mammalian Cells", Nature, vol. 385, pp. 810-813 (1997).

Hasty, Paul et al., "The Roel and Fate of DNA Ends for Homologous Recombination in Embryonic Stem Cells", Molecular and Cellular Biology, vol. 12:6, pp. 2464-2474 (1992).

Deng, Chuxia et al., "Reexamination of Gene Targeting Frequency as a Function of the Extent of Homology Between the Targeting Vector and the Target Locus", Molecular and Cellular Biology, vol. 12:8, pp. 3365-3371 (1992).

Thomas, Kirk R. et al., "High-Fidelity Gene Targeting in Embryonic Stem Cells by Using Sequence Replacement Vectors", Molecular and Cellular Biology, vol. 12:7, pp. 2919-2923 (1992).

Mortensen, Richard M et al., "Production of Homozygous Mutant ES Cells with a Single Targeting Construct", Molecular and Cellular Biology, vol. 12:5, pp. 2391-2395 (1992).

Casano, Francesca J et al., "The Structure and Complete Nucleotide Sequence of the Murine Gene Encoding Interleukin 1β Converting Enzyme (ICE)", Genomics, vol. 20, pp. 474-481 (1994).

Yeh, MY et al., "A Cell-Surface Antigen Which is Present in the Ganglioside Fraction and Shared by Human Meloanomas", Int J Cancer, vol. 29, pp. 269-275 (1982).

Kay, Mark A et al., "Hepatic Gene Therapy: Persistent Expression of Human ? 1-Antitrypsin in Mice after Direct Gene Delivery in Vivo", Human Gene Therapy, vol. 2, pp. 641-647 (1992).

Edlund, Thomas et al., Cell-Specific Expression of the Rat Insulin Gene: Evidence for Role of Two Distinct 5' Flanking Elements, Science, vol. 230, pp. 912-230 (1985).

Queen, Cary et al., "Immunoglobulin gene Transcription is Activated by Downstream Sequence Elements", Cell, vol. 33, pp. 741-748 (1983).

Banerji, Julian et al., "A Lymphocyte-Specific Cellular Enhancer is Located Downstream of the Joining Region in Immunoglobin Heavy Chan Genes", Cell, vol. 33, pp. 729-740 (1983).

Calame, Kathryn et al., "Transcriptional Controlling Elements in the Immunoglobulin and T Cell Receptor Loci", Advances in Immunolgy, vol. 43, pp. 235-275 (1988).

Pinkert, Carl et al., "An Albumin Enhancer Located 10kb Upstream Functions along with its Promoter to Direct Efficient, Liver-Specific Expression in Transgenic Mice", Gene & Development, vol. 1, pp. 268-276 (1987).

Ng, Sun-Yu et al., "Evolution of the Functional Human β-Action Gene and its Multi-Pseudogene Family: Conservation of Noncoding Regions and Chromosomal dispersion of Pseudogenes", Molecular and Cellular Biology, vol. 5:10, pp. 2720-2732 (1985).

Boshart, Michael et at., "A very Strong Enhancer is Located Upstream of an Immediate Early Gene of Human Cytomegalovirus", Cell, vol. 41, pp. 521-530 (1985).

Wakayama, Teruhiko et al., "Mouse Cloning with Nucleus Donor Cells of Donor Cells of Different Age Type", Molecular Reproduction and Development, vol. 58, pp. 376-383 (2001).

Thomas, Kirk et al., "Site-Directed Mutagenesis by Gene Targeting in Mouse Embryo-Derived Stem Cells", Cell, vol. 51, pp. 503-512 (1987).

Thomas, Kirk et al., "High Frequency Targeting of Genes to Specific Sites in the Mammalian Genome", Cell, vol. 44, pp. 419-428 (1986).

Nett, Michelle A et al., "Molecular Cloning of the Murine IL-1β Converting Enzyme cDNA", The Journal of Immunology, vol. 149, pp. 3254-3259 (1992).

Camper, Sally A, et al., "Postnatal Repression of the a-Fetoprotein Gene is Enhancer Independent", Genes & Development, vol. 3, pp. 537-546 (1989).

Joyner Alexandra L. et al., "Production of a Mutation in Mouse En-2 Gene by Homologous Recombination in Embryonic Stem Cells", Nature, vol. 338, pp. 153-156 (1989).

Sauer, Brian, "Inducible Gene Targeting in Mice Using the Cre/lox System", Methods: A Companion to Methods in Enzymology, vol. 14, pp. 381-392 (1998).

Johnson Bo, et al., "Comparison of Methods for Immobilization to Carboxymethyl Dextran Sensor Surfaces by Analysis of the Specific Activity of Monoclonal Antibodies", Journal of Molecular Recognition, vol. 8, pp. 125-131 (1995).

Bocher W.O. et al., "Antigen-Specific B and T Cells in Human/Mouse Radiation Chimera Following Immunization in Vivo" Immunology, vol. 96, pages 634-641 (1999).

Yeh, Ming-Yang et al., "Cell Surface Antigens of Human Melanoma Identified by Monoclonal Antibody", Proc Natl Acad Sci, vol. 76, pp. 2927-2931 (1979).

Jonsson, U et al., "Introducing a Biosensor Based Technology for Real Time Biospecific Interaction Analysis", Ann Biol Clin, vol. 51, pp. 19-26 (1993).

McKnight, Steven L et al., "The Distal Transcription Signals of the Herpesvirus tk Gene Share a Common Hexanucleotide Control Sequence", Cell, vol. 37, pp. 253-262 (1984).

Li, En et al, "Targeted Mutation of the DNA Methyltransferase Gene Results in Embryonic Lethality", Cell, vol. 69, pp. 915-926 (1992).

Berkner Kathleen L et al, "Development of Adenovirus Vectors for the Expression of Heterologous Genes", BioTechniques, vol. 6:7, pp. 616-629 (1988).

Rosenfeld Melissa A., "Adenovirus-Medicated Transfer of a Recombinant al-Antitrypsin Gene to the Lung Epithelium in Vivo", Science Reports, vol. 19, pp. 431-434 (1991).

Ward, E Sally et al., "Binding Activities of a Repertoire of Single Immunoglobulin Variable Domains Secreted from *Escherichia coli*", Nature, vol. 341, pp. 544-546 (1989).

Skarnes, William C et al., "A Gene Trap Approach in Mouse Embryonic Stem Cells: the lacZ Reporter is Activated by Splicing, Reflects Endogenous Gene Expression, and is Mutagenic in Mice", Gene & Development, vol. 6, pp. 903-918 (1992).

Capecchi, Mario R et al., "Altering the Genome by Homologous Recombination", Science, vol. 244, pp. 1288-1292 (1989).

Wakayama, T et al., "Full-Term Development of Mice from Enucleated Oocytes Injected with Cumulus Cell Nuclei", Nature, vol. 394, pp. 369-374 (1998).

McCreath, KJ et al., "Production of Gene-Targeted Sheep by Nuclear Transfer from Cultured Somatic Cells", Nature, vol. 405, pp. 1066-1069 (2000).

Wu, Hong et al., "Double Replacement: Strategy for Efficient Introduction of Subtle Mutations into the Murine Colla-1 Gene by Homologous Recombination in Embryonic Stem Cells", Proc Natl Acad Sci, vol. 91, pp. 2819-2823 (1994).

Ikeda, Seiski et al., An AquaporinLike Gene Required for the Brassica Self-Incompatibility Response, Science, vol. 276, pp. 1564-1566 (1997).

Kato, Yoko et al., "Eight Calves Cloned from Somatic Cells of a Single Adult", Science, vol. 282, pp. 2095-2098 (1998).

Ilan, Ehud et al., "The Hepatitis B Virus-Trimera Mouse: A Model for Human HBV Infection and Evaluation of Anti-HBV Therapeutic Agents", Hepatology, vol. 29, pp. 553-562 (1999).

Taylor, Gregory A et al., "Identification of a Novel GTPase, the Iducibly Expressed GTPase, that Accumulates in Response to Interon", The Journal of Biological Chemistry, vol. 271:34, pp. 20399-20405 (1996).

Reisner, Yair et al., The Trimera Mouse: Generating Human Monoclonal Antibodies and an Animal Model for Human Diseases, Tibtech, vol. 16, pp. 242-246 (1989).

Min Deng, Jian et al., "An Insertional Mutation in the BTF3 Transcription Factor Gene Leads to an Early Postimplantation Lethality in Mice", Transgenic Research, vol. 4, pp. 264-269 (1995).

Fagerstam, Jonsson L et al., Real-Time Biospecific Interaction Analysis Using Surface Plasmon Resonance and a Sensor Chip Technology, BioTechniques, vol. 11:5, pp. 620-627 (1991).

Kipriyanov, Sergey M et al., "Recombinant Single-Chain Fv Fragments Carrying C-Terminal Cysteine Residues: Production of Bivalent and Biotinylated Miniantibodies", Molecular Immunology, vol. 31:12, pp. 1047-1058 (1994).

Poljak, Roberto J et al., "Production and Structure of Diabodies", Structure, vol. 2, pp. 1121-1123 (1994).

Gefter, Malcolm L et al., "A Simple Method for Poyethylen Glycol_Promoted Hybridiaztion of Mouse Myeloma Cells", Somatic Cell Genetics, vol. 3, pp. 231-236 (1977).

Wu, George Y et al., "Receptor-Mediated Gene Delivery and Expression", The Journal of Biological Chemistry, vol. 263:29, pp. 14621-14624 (1988).

Acsadl, Gyula et al., "Human Dystrophin Expression in MDX Mice after Intramuscular Injection of DNA Constructs", Nature, vol. 352, pp. 815-818, (1991).

Zelenin, Alexander V et al., "Transfer of Foreign DNA into the Cell of Developing Mouse Embryos by Microprojectile Bombardment", FEBS, vol. 315:1, pp. 29-31 (1993).

Eren, R et al., "Human Monoclonal Antibodies Specific to Hepatitis B Virus Generated in a Human/Mouse Radiation Chimera: the Trimera system", Immunology, vol. 92, pp. 154-161.

Kohler, G et al., "Continuous Cultures of Fused Cells Secreting Antibody of Predefiend Specificity", Nature, vol. 256, pp. 495-497 (1975).

Galfre, G et al., "Antibodies to Major Histocompatibilitiy Antigens Produced by Hybrid Cell Lines", Nature, vol. 266, pp. 550-552 (1977).

Brown, Joseph P et al., "Structural Characterization of Human Melanoma-Associated Antigen p97 with Monoclonal Antibodies", The Journal of Immunolgy, vol. 127:2, pp. 539-546 (1981).

Brown, Joseph P et al., "Protein Antigens of Normal and Malignant Human Cells Identified by Immunoprecipitation with Monoclonal Antibodies", The Journal of Biological Chemistry, vol. 255, pp. 4980-4983 (1980).

Tratschin, Jon-Duri, et al., "Adeno-associated Virus Vector for High-Frequency Integration, Expression, and Rescue of Genes in Mammalian Cells", Molecular and Cellular Biology, vol. 5:11, pp. 3251-3260 (1985).

Gossler, Achim et al, "Mouse Embryonic Stem Cells and Reporter Constructs to Detect Developmental Regulated Genes", Science Reports, vol. 244, pp. 463-465 (1989).

* cited by examiner

US 7,795,494 B2

TRANSGENIC MICE EXPRESSING ANTIBODIES SPECIFIC FOR GENES OF INTEREST AND USES THEREOF

CROSS-REFERENCE TO RELATED APPLICATION

This application claims priority to U.S. provisional application No. 60/278,515, filed Mar. 22, 2001.

RELATED INFORMATION

The contents of all patents, patent applications, and references cited throughout this specification are hereby incorporated by reference in their entireties.

BACKGROUND OF THE INVENTION

The notion that antibodies provide a specific, safe and rapid means to develop therapeutics is gaining momentum. With the human genome project almost completed, a large number of novel antibody targets are available. Well established methodologies to make monoclonal antibodies (mAbs) are available as well. These methodologies include both in vitro (phage display, yeast display, viral display etc) and in vivo (immunizations of animals with the target antigen followed by classical hybridoma technology) approaches. Therapeutic antibodies can be fully human, humanized or CDR-grafted. It is believed that of these antibodies, fully-human therapeutic antibodies show most promise as they might be less immunogenic and have a long half-life.

Transgenic (Tg) mice carrying human genes encoding antibodies offer a method of making fully human mAbs rapidly. However, one of the main limitations of this approach is that a large number of proteins are highly conserved, both structurally and functionally, between humans and rodents. In the case of conserved proteins, the majority of antibodies raised would be against regions (epitopes) of proteins that are dissimilar between human and mice. Such regions may or may not yield neutralizing, therapeutic grade mAbs.

SUMMARY OF THE INVENTION

The invention provides non-human transgenic animals containing alterations in a gene of interest such that the product of the gene of interest is not expressed. The absence of the product of the gene of interest in the animal allows the production of immunoglobulin molecules by the animal, upon exposure to the product of the gene of interest (GOI). The present invention thus provides methods for producing immunoglobulin molecules which overcome the problems of generating antibodies against highly conserved proteins (i.e., genes of interest) that may be recognized as self in a non-human animal and would thus be non-immunogenic.

In a preferred embodiment (1), the invention provides a non-human transgenic animal containing a mutation in a gene of interest (GOI) such that the corresponding gene product is no longer produced, and when this animal is exposed to the gene product it is capable of expressing an immunoglobulin molecule which can bind the gene product. In embodiment (2), the animal is capable of expressing a functional immunoglobulin that can bind the human homolog of the GOI product. In embodiment (3), the non human transgenic animal is also transgenic for human immunoglobulins and is therefore capable of expressing a functional human immunoglobulin which can bind the human homolog of the GOI product. In embodiment (4), the immunoglobulin can be a human heavy chain, a human light chain, or both a human heavy chain and a human light chain. In embodiment (5), at least one endogenous immunoglobulin locus is inactivated in the non-human transgenic animal.

In another preferred embodiment (6), the invention provides a non-human transgenic animal containing the following: (a) at least one inactivated endogenous immunoglobulin locus; (b) carrying nucleic acid encoding at least a portion of a human immunoglobulin capable of being expressed as a functional binding molecule; (c) containing an alteration in a gene of interest such that the corresponding gene product is no longer produced; such that this animal, upon exposure to the gene product, can express a functional human immunoglobulin capable of binding the gene product. In embodiment (7), the endogenous immunoglobulin locus consists of an endogenous heavy chain, an endogenous light chain or both. In embodiment (8) the non human animal contains nucleic acid for human heavy chain, a human light chain, or both.

In preferred embodiment (9), the invention provides a non-human transgenic animal containing the following: (a) inactivated endogenous heavy chain and light chain immunoglobulin loci; (b) nucleic acid encoding heavy and light chains of human immunoglobulin which can express a functional antibody; (c) an alteration in a gene of interest such that the corresponding gene product is no longer produced; such that this animal upon exposure to the gene product, is capable of expressing a human light chain and human heavy chain as a functional human immunoglobulin which can bind the gene product. In embodiment (10) the non-human transgenic animal according to embodiment 6 and 9, when exposed to the human homolog of the gene product is capable of expressing a functional human immunoglobulin capable of binding the gene product.

In embodiment (II), the antibodies expressed by the non-human transgenic animals of all the foregoing embodiments can be IgG, IgM or IgA. In embodiment (12) the alteration in the GOI in the animal in all the foregoing embodiments can be a naturally occurring disruption, a genetically engineered disruption or excision of the gene. In embodiment (13) the GOI in all the foregoing embodiments can be any protein, polypeptide or peptide which may or may not further acquire glycosylation, phosphorylation etc. by posttranslational modification. In embodiment (14) these proteins, polypeptides and peptides are secreted proteins or surface receptors. According to embodiment (15) the secreted proteins may be selected from families of cytokines such as interferon (IFN), tumor necrosis factor (TNF), Interleukins (IL), IP-10, PF4, a GRO, 9E3, EMAP-II, colony stimulating factor (CSF), fibroblast growth factor (FGF), and platelet derived growth factor (PDGF). Further in embodiment (16) the interleukins could be IL-1α; IL-1β, IL-12 or IL-18. In a preferred embodiment, the endogenous GOI is the IL-18 gene.

In embodiment (17) an antibody and any fragment of the antibody capable of binding the gene product of the GOI can be derived from the non human transgenic animal of all the foregoing embodiments. In embodiment (18) nucleic acid encoding the antibody can be derived from the non human transgenic animal. In embodiment (19) B cells expressing the antibody can be derived from the non human transgenic animal and subsequently used to derive hybridomas which can express a monoclonal antibody capable of binding the gene product. In embodiment (20) embryonic stem cells can be derived from the non human transgenic animal of the foregoing embodiments. In embodiment (21) progeny can also be derived from the non human transgenic animal of the foregoing embodiments.

In preferred embodiment (22), the invention provides a method of making a non-human transgenic animal from embryonic stem cells wherein the endogenous gene of interest is altered such that the product of this endogenous gene can no longer be produced; this animal, upon exposure to the gene product, can express antibodies capable of binding the gene product.

In embodiment (23) the invention provides another method of making a non-human transgenic animal from embryonic stem cells wherein multiple endogenous genes of interest are altered such that the products of these endogenous genes can no longer be produced such that the animal, upon exposure to these gene products can express antibodies capable of binding the gene products. In embodiment (24), the gene product according to embodiments 22 and 23 is a human homolog. In embodiment (25), the non human transgenic animal of the foregoing embodiments 22 and 23 is also transgenic for human immunoglobulin genes such that upon exposure to the human homolog of the gene product the animal is capable of expressing a functional human antibody capable of binding the human gene product. In embodiment (26), the immune system of the non human transgenic animal from embodiment 22 and 23 can be ablated and subsequently engrafted with bone marrow cells capable of expressing human immunoglobulins.

In preferred embodiment (27) the invention provides another method of making progeny by mating non-human animal transgenic for human immunoglobulin genes with non human transgenic animal wherein one or more of the animal's genes of interest are altered such that one or more of the endogenous gene products of the genes of interest are no longer produced and its progeny upon exposure to a gene product or its human homologue, is capable of expressing a human immunoglobulin which can bind the gene product.

In preferred embodiment (28) the invention provides a method of making a non-human transgenic animal from an embryonic stem cell which already carries the human immunoglobulin genes; where one or more endogenous genes of interest have been altered such their gene products are no longer produced; such that this animal, upon exposure to one or more of the gene products or their human homolog, can express human immunoglobulins capable of binding the gene products. In a preferred embodiment the GOI in all the foregoing embodiments can be any protein, polypeptide or peptide. Further these proteins, polypeptides and peptides can be secreted proteins or surface receptors. In a more preferred embodiment, the secreted proteins may be selected from families of cytokines such as interferon (IFN), tumor necrosis factor (TNF), Interleukins (IL), IP-10, PF4, a GRO, 9E3, EMAP-II, colony stimulating factor (CSF), fibroblast growth factor (FGF), and platelet derived growth factor (PDGF). In a most preferred embodiment, the interleukins could be IL-1α, IL-1β, IL-12 or IL-18. In the foregoing embodiments wherein antibodies with multiple specificities capable of recognizing a combination of antigens are obtained, such combination of antigens may include two or more of the gene products of genes of interest mentioned above.

In embodiment (29) the non-human transgenic animal in all the foregoing embodiments can be a mouse, rat, rabbit or goat. The most preferred animal of the foregoing group is a mouse.

In embodiment (30) the invention provides a method of treating disease in a patient in need thereof by administering the monoclonal antibody of foregoing embodiment 20 to the patient. In embodiment (31) the invention provides a method of diagnosing disease by using the monoclonal antibody of embodiment 20 to detect the antigen in a sample from the patient. In embodiment (32) the invention provides a method of detecting the presence of disease by administering the monoclonal antibody of embodiment 20 to a patient and imaging the binding of the monoclonal antibody to a particular antigen associated with the disease.

In preferred embodiment (33) the invention provides a method of producing a binding molecule capable of binding the gene product of a gene of interest wherein the binding molecule is encoded by a nucleic acid derived from a library of organisms, each organism displaying at its surface an immunoglobulin; and each organism containing nucleic acid with sequence derived from a non-human transgenic animal of all foregoing embodiments unimmunized with the gene of interest antigen and not having immunoglobulin molecules specific for the gene of interest antigen found in the sera, and encoding a polypeptide chain which is a component part of the immunoglobulin displayed at the surface of that organism; and selecting, by binding with the gene product, one or more immunoglobulins with binding specificity for the gene product. In embodiment (34) the invention provides a method of screening binding partners of the immunoglobulin utilizing differential display with phage, yeast or viral systems. In another embodiment (35) the invention provides a method of making a binding molecule of the immunoglobulin, utilizing differential display with phage, yeast or viral systems.

In embodiment (36) the invention provides a method for synthesizing a DNA library capable of encoding a family of binding proteins by performing the following steps:
  (a) isolating DNA encoding a diverse set of antigen binding proteins from a tissue sample from the non-human transgenic animal of all foregoing embodiments
  (b) amplifying the specific gene sequences using primers specific for the conserved regions of the DNA
  (c) inserting the amplified DNA into the variable region area of a framework antibody expression vector that has a substantial portion of the immunoglobulin heavy chain gene,
  (d) expressing the vector from step (c) with a vector containing an immunoglobulin light chain gene and transfecting the vectors into a cell, so as to create a library of cells producing both light chain immunoglobulins and heavy chain immunoglobulins.

Advantages of the above transgenic animals and methods include the ability to generate fully human immunoglobulin molecules specific for a particular gene of interest. The present invention further provides methods of producing the immunoglobulin molecules in the non-human transgenic animals and methods of using the molecules.

Other features and advantages of the invention will be apparent from the following detailed description and claims.

DETAILED DESCRIPTION OF THE INVENTION

Humans and animals are naturally tolerant to all self proteins. This tolerance occurs because immune cells that recognize self-proteins are deleted during development. In addition, peripheral tolerance mechanisms keep in check self-reactive immune cells. This immune tolerance to self proteins serves to limit the antibody repertoire of B and T cells to highly homologous proteins in animals such that antibodies may be raised only against regions of nonidentity. However, if animals are deficient in the protein(s) of interest, they would not develop tolerance to the protein and would be able to mount an immune response to the entire protein. Such animals would therefore offer an ideal means to generate an immune response to the protein of interest leading to effective high affinity monoclonal antibodies to the entire protein. Animals lacking specific protein(s) can be generated by targeted gene disruption/deletion technology. Mouse is the preferred animal for the foregoing purpose.

The present invention is based, at least in part, on the generation of novel non-human transgenic animals containing an alteration in a gene of interest such that its product is not produced. In a preferred embodiment, such animals will lack endogenous Ig genes and express human Ig transgenes. These novel non-human transgenic animals are capable of, for example, generating antibodies, e.g., human antibodies, specific for the product of a gene of interest that has been functionally disrupted in the animal.

The term "gene of interest" (GOI), as used herein, refer to an endogenous gene in a non-human animal. The GOI may be functionally disrupted such that the normal function of the GOI is prevented.

The terms "functionally disrupted", "alteration in a gene of interest", and "inactivated" as used herein, refer to a gene that has a mutation that prevents the normal function of the gene, e.g., prevents expression of a normal Ig gene and/or a gene of interest product or prevents expression of normal amounts of the Ig gene and/or a gene of interest product. The mutation causing the functional disruption can be an insertion, deletion or point mutation(s) which alter the amino acid sequence of the endogenous GOI and/or endogenous Ig gene product encoded therein.

The term "substantially reduced or absent" is intended to mean that essentially undetectable amounts of normal endogenous GOI product and/or endogenous Ig gene product are produced in cells of the animal. This type of mutation is also referred to in the art as a "null mutation" and an animal carrying such a null mutation is also referred to as a "knockout animal".

The term "transgenic animal", as used herein, refers to an animal having cells that contain a transgene, wherein the transgene was introduced into the animal or an ancestor of the animal at a prenatal, e.g., an embryonic, stage. A "transgene" is a DNA which is integrated into the genome of a cell from which a transgenic animal develops and which remains in the genome of the mature animal, thereby directing the expression of an encoded gene product in one or more cell types or tissues of the transgenic animal. In a preferred embodiment, the transgenes are the human IgG genes.

The mammalian immune system includes B lymphocytes that, in totality, express antibody repertoire composed of hundreds of billions of different antibody specificities. The normal "immune response" to a particular antigen involves the selection from this repertoire of one or more antibodies that specifically bind the antigen, and the success of an immune response is based, at least in part, on the ability of these antibodies to specifically recognize the stimulating antigen and "ignore" other molecules in the environment of the antibodies.

The terms "immunoglobulin" and "antibody", as used herein, are intended to refer to immunoglobulin molecules comprised of four polypeptide chains, two heavy (H) chains and two light (L) chains inter-connected by disulfide bonds. As used herein, the term "heavy chain" is the region of an antibody comprised of a heavy chain variable region (abbreviated herein as HCVR or VH) and a heavy chain constant region. The heavy chain constant region is comprised of three domains, CH1, CH2 and CH3. As used herein, the term "light chain" is the region of an antibody comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4.

A "monoclonal antibody", as used herein, is intended to refer to a hybridoma-derived antibody (e.g., an antibody secreted by a hybridoma prepared by hybridoma technology, such as the standard Kohler and Milstein hybridoma methodology). The monoclonal antibody may be specific for a single antigen or may be capable of binding more than one antigen. A hybridoma-derived dual specificity antibody of the invention is still referred to as a monoclonal antibody although it has antigenic specificity for more than a single antigen.

The term "human antibody", as used herein, refers to antibodies having variable and constant regions corresponding to, or derived from, human germline immunoglobulin sequences as described by, for example, Kabat et al. (See Kabat, et al. (1991) *Sequences of Proteins of Imunological Interest, Fifth Edition*, U.S. Department of Health and Human Services, NIH Publication No. 91-3242). The human antibodies of the invention, however, may include amino acid residues not encoded by human germline immunoglobulin sequences (e.g., mutations introduced by random or site-specific mutagenesis in vitro or by somatic mutation in vivo), for example in the CDRs and in particular CDR3.

Recombinant human antibodies of the invention have variable regions, and may also include constant regions, derived from human germline immunoglobulin sequences (See Kabat, E. A., et al. (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis or backmutation or both.

The term "chimeric antibody" refers to antibodies which comprise heavy and light chain variable region sequences from one species and constant region sequences from another species, such as antibodies having murine heavy and light chain variable regions linked to human constant regions.

An "isolated antibody," as used herein, is intended to refer to an antibody that is substantially free of other antibodies having different antigenic specificities (e.g., an isolated antibody that specifically binds a peptide or protein expressed by a GOI is substantially free of antibodies that specifically bind antigens other than the GOI product). An isolated antibody that specifically binds a GOI product may, however, have cross-reactivity to other antigens, such as GOI-encoded molecules from other species. Moreover, an isolated antibody may be substantially free of other cellular material and/or chemicals.

The term "functional immunoglobulin", as used herein, refers to antibodies capable of neutralizing the antigen (e.g., GOI product), acting as an agonist or antagonist for the antigen and any other change in the antigen which modifies the function of the antigen.

The term "cell," as used herein, refers to the smallest structure capable of independently carrying out life sustaining processes, including metabolic processes, e.g., growth, and reproduction. The term "cell," as used herein, includes a bacterial, yeast, fungal, plant, or animal cell.

The term "recombinant cell," as used herein, is intended to include a genetically modified cell. The cell can be a microorganism or a higher eukaryotic cell. The term is intended to include progeny of the cell originally modified. In preferred embodiments, the cell is a zygote or an embryonic stem cell. The term "germ cell," as used herein, includes haploid sperm cells, egg cells, and their precursors. The term "somatic cell," as used herein, includes any diploid cell in an organism that is not a germ cell.

A preferred non-human animal is characterized by: (1) being incapable of expressing an endogenous gene of interest; (2) being capable of producing xenogeneic immunoglobulin light and heavy chains to produce a xenogeneic immunoglobulin or immunoglobulin analog; (3) being incapable of producing endogenous immunoglobulin heavy chain; and (4) being substantially incapable of producing endogenous immunoglobulin light chains. Thus, the animal may have an entire endogenous immunoglobulin locus substituted by a portion of, or an entire, xenogeneic immunoglobulin locus, or may have a xenogeneic immunoglobulin locus inserted into a chromosome of the host cell and an inactivated endogenous immunoglobulin region. These various alternatives will be achieved, at least in part, by employing homologous recombination for inactivation or replacement at the immunoglobulin loci for the heavy and light chains.

I. Methods of Generating Transgenic Non-Human Animals Containing Altered Genes of Interest Functional disruption of an endogenous GOI and/or an endogenous Ig gene allele in a cell can be achieved by homologous recombination between the allele and a GOI gene and/or endogenous Ig gene, or portion thereof, introduced into the cell. The cell can be a differentiated cell type that normally expresses Ig, such as a B-cell, or a B-cell-like cell line (i.e., cell lines with the properties of these cell types, including the expression of Ig), or a cell that normally expresses the GOI. Alternatively, the cell can be a pluripotent progenitor cell that can develop into an animal, such as an embryonic stem cell. When the cell is an embryonic stem cell, the cell can be introduced into a blastocyst and the blastocyst allowed to develop in a foster animal to thereby produce an animal having somatic and germ cells in which an endogenous GOI gene allele and/or an endogenous Ig gene allele is functionally disrupted. Such an animal is referred to herein as a "homologous recombinant" animal. A preferred homologous recombinant animal of the invention is a mouse.

To create a homologous recombinant cell or animal, a targeting vector is prepared which contains DNA encoding a GOI and/or an Ig gene, or a portion thereof, having a mutation introduced therein. A preferred targeting vector for creating a null mutation in an endogenous GOI and/or an endogenous Ig gene includes GOI-encoding DNA and/or Ig-encoding DNA into which has been inserted non-GOI encoding DNA and/or non-Ig encoding DNA. For example, in one embodiment, a targeting vector of the invention for functionally disrupting an endogenous GOI and/or an Ig gene in a cell comprises:

a) a non-homologous replacement portion;
b) a first homology region located upstream of the non-homologous replacement portion, the first homology region having a nucleotide sequence with substantial identity to a first GOI and/or Ig gene sequence; and
c) a second homology region located downstream of the non-homologous replacement portion, the second homology region having a nucleotide sequence with substantial identity to a second GOI and/or Ig gene sequence, the second GOI and/or Ig gene sequence having a location downstream of the first GOI and/or Ig gene sequence in a naturally occurring endogenous GOI and/or endogenous Ig gene.

Thus, the non-homologous replacement portion is flanked 5' and 3' by nucleotide sequences with substantial identity to the GOI and/or Ig gene sequences. A nucleotide sequence with "substantial identity" to a GOI and/or an Ig gene sequence is intended to describe a nucleotide sequence having sufficient homology to a GOI and/or an Ig gene sequence to allow for homologous recombination between the nucleotide sequence and an endogenous GOI and/or an endogenous Ig gene sequence in a host cell. Typically, the nucleotide sequences of the flanking homology regions are at least 80%, more preferably at least 90%, even more preferably at least 95%, and most preferably 100% identical to the nucleotide sequences of the endogenous GOI and/or endogenous Ig gene to be targeted for homologous recombination. Most preferably, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous GOI and/or an endogenous Ig gene in a host cell when the vector is introduced into the host cell. Typically, the flanking homology regions are at least 1 kilobase in length and more preferably are least several kilobases in length.

A typical targeting vector has a positive selection expression cassette as the non-homologous replacement portion. The term "positive selection expression cassette" refers to nucleotide sequences encoding a positive selection marker operatively linked to regulatory elements that control expression of the positive selection marker (e.g., promoter and polyadenylation sequences). A "positive selection marker" allows for selection of cells which contain the marker, whereas cells that do not contain and express the marker are selected against (e.g., are killed by the selecting agent). For example, a preferred positive selection expression cassette includes a neomycin phosphotransferase ("neo") gene operatively linked to a promoter and a polyadenylation signal. Cells carrying and expressing the neo gene exhibit resistance to the selecting agent G418.

In addition to the positive selection expression cassette, a targeting vector of the invention typically also includes a negative selection expression cassette located distal to either the upstream or downstream homology regions (i.e., the regions substantially identical to Ig-encoding sequences). A "negative selection expression cassette" refers to nucleotide sequences encoding a negative selection marker operatively linked to regulatory elements that control expression of the negative selection marker. A "negative selection marker" allows for selection against cells which carry the marker, e.g., cells that contain and express the marker are killed by a selecting agent, whereas cells that do not contain and express the negative selection marker survive. For example, a preferred negative selection expression cassette includes a herpes simplex virus thymidine kinase ("tk") gene operatively linked to a promoter and a polyadenylation signal. Cells that contain and express the tk gene can be killed, for example, by the selecting agent gancyclovir.

This configuration of the targeting vector allows for use of the "positive/negative" selection technique for selecting homologous recombinants: cells into which the targeting vector has been introduced are selected that contain and express the positive selection marker but which have lost the negative selection marker. Accordingly, these cells carry the non-homologous replacement portion DNA (e.g., the inserted neo gene) but have lost the DNA encoding the negative selection marker located distal thereto in the targeting vector, likely as a result of homologous recombination between the targeting vector and the endogenous Ig gene.

In a preferred embodiment, the targeting vector includes flanking homology regions having substantial identity to a mouse GOI and/or mouse Ig (mIg) gene sequences to thereby target an endogenous mouse GOI and/or an endogenous mouse Ig gene in a mouse host cell (e.g., a murine embryonic stem cell) for homologous recombination. Murine GOI and/or murine Ig genomic DNA used as the flanking homology regions of the targeting vector can be isolated from a murine genomic DNA library by screening the library with a cDNA probe encompassing all or part of the murine GOI cDNA and/or the murine Ig cDNA using standard techniques. Preferably, a genomic DNA library screened is prepared from cells isogenic with the cell to be transfected with the targeting vector. For example, a genomic library from the 129/Sv strain of mouse (available commercially from Stratagene) can be screened to isolate mouse Ig genomic DNA for use in a targeting vector for transfection into the D3 embryonic stem cell line derived from strain 129/Sv. The nucleotide sequence of the mouse Ig cDNA and predicted amino acid sequence of the mouse Ig protein are disclosed in Nett et al. (1992) *J. Immunol.* 149:3254-3259. The structure and complete nucleotide sequence of the murine Ig gene are disclosed in Casano, F. J. et al. (1994) *Genomics* 20:474-481.

To functionally disrupt an endogenous GOI and/or an endogenous Ig gene allele in a host cell, a targeting vector of the invention is introduced into the host cell, e.g., a differentiated cell that normally expresses the GOI and/or the Ig, or an embryonic stem cell, and homologous recombinants are selected. A targeting vector can be introduced into a host cell by any of several techniques known in the art suitable for the introduction of exogenous DNA (e.g., calcium phosphate precipitation, DEAE-dextran transfection, microinjection, lipofection and the like) but is most preferably introduced into the host cell by electroporation. After introduction of the vector into the host cell, the cell is cultured for a period of time and under conditions sufficient to allow for homologous recombination between the introduced targeting vector and an endogenous GOI and/or an endogenous Ig gene. Host cells are selected (e.g., by the positive/negative selection techniques described above) and screened for homologous recombination at the endogenous GOI and/or the endogenous Ig gene locus by standard techniques (e.g., Southern hybridizations using a probe which distinguishes the normal endogenous allele from the homologous recombinant allele).

To create a cell (e.g., macrophage or a monocyte) homozygous for the GOI and/or the Ig gene disruption, the G418 escalation method of Mortensen, R. N. et al. ((1992) *Mol. Cell. Biol.* 12:2391-2395) can be used on the heterozygous cells. Alternatively, the first allele of a wild type host cell can be disrupted by a first homologous recombination event that is selected with one marker (e.g., G418 resistance) and then the second allele of the heterozygous cells can be disrupted by a second homologous recombination event that is selected with a different marker (e.g., hygromycin resistance) (see e.g., TeRiele, H. (1990) *Nature* 348:649-651).

To create a homologous recombinant animal of the invention, an embryonic stem cell having one GOI and/or Ig gene allele functionally disrupted is introduced into a blastocyst, the blastocyst is implanted into a pseudopregnant foster mother, and the embryo allowed to develop to term. The resultant animal is a chimera having cells descendant from the embryonic stem cell. Chimeric animals in which the embryonic stem cell has contributed to the germ cells of the animal can be mated with wild type animals to thereby produce animals heterozygous for the GOI and/or the Ig gene disruption in all somatic and germ cells. The heterozygous animals can then be mated to create animals homozygous for the Ig gene disruption (i.e., having both GOI and/or Ig gene alleles functionally disrupted). These homologous recombinant animals mentioned above can be used as control or test animals for in vivo screening assays (described further in detail below). Additionally, cells of the animal homozygous for the GOI and/or the Ig gene disruption can be isolated from the animals and cultured for use in in vitro screening assays. For example, peritoneal exudate macrophages (e.g., thioglycolate-elicited), which normally express Ig, can be isolated from the animals by standard techniques. Furthermore, immortalized cell lines can be prepared from cells of the animal using standard techniques for cell immortalization, e.g., by transfection of the cells with an expression vector encoding myc, ras or SV40 large T antigen.

For additional descriptions of targeting vectors and homologous recombination methodologies, see also e.g., Thomas, K. R. et al. (1986) *Cell* 44:419-428; Thomas, K. R. et al. (1987) *Cell* 51:503-512; Thomas, K. R. et al. (1992) *Mol. Cell. Biol.* 12:2919-2923; Deng, C. and Capecchi, M. R. (1992) *Mol. Cell. Biol.* 12:3365-3371; Hasty, P. et al. (1992) *Mol. Cell. Biol.* 12:2464-2474; Li, E. et al. (1992) *Cell* 69:915; Zhang, H., et al. (1994) *Mol. Cell. Biol.* 14:2404-2410; Bradley, A. in *Teratocarcinomas and Embryonic Stem Cells: A Practical Approach*, E. J. Robertson, ed. (IRL, Oxford, 1987) pp. 113-152; PCT International Publication No. WO 90/11354; PCT International Publication No. WO 91/01140; PCT International Publication No. WO 91/19796; PCT International Publication No. WO 92/20808; and PCT International Publication No. WO 93/04169. Alternatively, nuclei from somatic cells which are heterozygous or homozygous for the GOI and/or the Ig gene disruption can be introduced into enucleated unfertilized eggs and subsequently implanted into pseudopregnant foster mothers to generate homologous recombinant animals, see also e.g., Wilmut, I. et al. (1997) *Nature* 385(6619):810-813; Kato, Y. et al. (1998) *Science* 282(5396):2095-2098; Wakayama, T. et al. (1998) *Nature* 394(6691):369-374; McCreath, K. J. et al. (2000) *Nature* 405(6790):1066-1069; Wakayama, T. et al (2001) *Mol. Reprod. Dev.* 58(4):376-383. Both copies of an Ig gene can be functionally disrupted according to the methods described in PCT International Publication WO 93/16177. Additionally, a recombinase can be used to functionally disrupt a GOI and/or an Ig gene by homologous recombination as described in PCT International Publication WO 93/22443.

In addition to allowing for introduction of a null mutation in a gene allele (e.g., an Ig and/or GOI allele), similar techniques can be used to introduce insertions, point mutations or deletions into a gene allele (e.g., an Ig and/or GOI allele). Point or deletion mutations can be introduced into a gene allele by, for example, the "hit and run" homologous recombination procedure (as described in Valancius, V. and Smithies, O. (1991) *Mol. Cell. Biol.* 11:1402-1408; and Hasty, P. et al. (1991) *Nature* 350:243-246) or by the double replacement homologous recombination procedure (as described in Wu, H. et al. (1994) *Proc. Natl. Acad. Sci. USA* 91:2819-2823). Accordingly, in another embodiment, the invention provides homologous recombinant cells and animals (e.g., human cells or non-human animals) that express an altered Ig gene and/or GOI product.

To create a transgenic animal, a nucleic acid of the invention encoding a transactivator fusion protein, as described above, can be incorporated into a recombinant expression vector in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by viral genetic material. For example, commonly used promoters are derived from polyoma, adenovirus 2, cytomegalovirus and simian virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. For example, an expression vector similar to that described in Example 1 can be used. The human cytomegalovirus IE promoter is described in Boshart et al. (1985) *Cell* 41:521-530. Other ubiquitously expressing promoters which can be used include the HSV-Tk promoter (disclosed in McKnight et al. (1984) *Cell* 37:253-262) and β-actin promoters (e.g., the human β-actin promoter as described by Ng et al. (1985) *Mol. Cell. Biol.* 5:2720-2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Alternatively, a self-regulating construct encoding a transactivator fusion protein can be created. To accomplish this, nucleic acid encoding the fusion protein is operatively linked to a minimal promoter sequence and at least one tet operator sequence. When this nucleic acid is introduced into a cell (e.g., in a recombinant expression vector), a small amount of basal transcription of the transactivator gene is likely to occur due to "leakiness". In the presence of tetracycline Tc (or analog thereof) this small amount of the transactivator fusion protein will bind to the tet operator sequence(s) upstream of the nucleotide sequence encoding the transactivator and stimulate additional transcription of the nucleotide sequence encoding the transactivator, thereby leading to further production of the transactivator fusion protein in the cell. It will be appreciated by those skilled in the art that such a self-regulating promoter can also be used in conjunction with other tetracycline-regulated transactivators, such as the wild-type Tet repressor fusion protein (tTA) described in Gossen, M. and Bujard, H. (1992) *Proc. Natl. Acad. Sci. USA* 89:5547-5551, which binds to tet operators in the absence of Tc (as illustrated in FIG. 9A). When used in conjunction with this transactivator, self-regulated transcription of the nucleotide sequence encoding this transactivator is stimulated in the absence of Tc. The plasmid pUHD15-3, which comprises nucleotide sequences encoding the tTA described in Gossen and Bujard (1992), cited supra, operatively linked to a self-regulating promoter, has been deposited on Jul. 8, 1994 under the provisions of the Budapest Treaty at the Deutsche Sammlung Von Mikroorganismen und Zell Kulturen GmbH (DSM) in Braunschweig, Germany and assigned deposit number DSM 9280.

In one embodiment, the recombinant expression vector of the invention is a plasmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψA m. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251-3260 can be used to express a transactivator fusion protein.

Nucleic acid encoding fusion proteins can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual,* 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transfected with one or more nucleic acids which serve as the target for the fusion protein. The target nucleic acid comprises a nucleotide sequence to be transcribed operatively linked to at least one tet operator sequence.

Nucleic acid encoding the fusion protein of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377-8381; and Kay, M. A. et al. (1992) *Human Gene Therapy* 3:641-647), adenoviral vectors (see e.g., Rosenfeld, M. A. (1992) *Cell* 68:143-155; and Herz, J. and Gerard, R. D. (1993) *Proc. Natl. Acad. Sci. USA* 90:2812-2816), receptor-mediated DNA uptake (see e.g., Wu, G. and Wu, C. H. (1988) *J. Biol. Chem.* 263:14621; Wilson et al. (1992) *J. Biol. Chem.* 267:963-967; and U.S. Pat. No. 5,166,320), direct injection of DNA (see e.g., Acsadi et al. (1991) *Nature* 332:815-818; and Wolff et al. (1990) *Science* 247:1465-1468) or particle bombardment (see e.g., Cheng, L. et al. (1993) *Proc. Natl. Acad. Sci. USA* 90:4455-4459; and Zelenin, A. V. et al. (1993) *FEBS Letters* 315:29-32). Thus, for gene therapy purposes, cells can be modified in vitro and administered to a subject or, alternatively, cells can be directly modified in vivo.

The nucleic acid transactivator fusion protein can be transferred into a fertilized oocyte of a non-human animal to create a transgenic animal which expresses the fusion protein of the invention in one or more cell types. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming"). In still another embodiment, the transgenic animal is a non-human primate.

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. Transgenic animals carrying a transgene encoding the fusion protein of the invention can further be bred to other transgenic animals carrying other transgenes, e.g., to a transgenic animal which contains a gene operatively linked to a tet operator sequence.

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

The features and characteristics of the animals of the invention, and cells derived therefrom, make them useful for a wide variety of applications, as described in further detail in the subsections below.

II. Use of Non-human Transgenic Animals for Making Antibodies

The invention provides antibodies, as well as antibody portions thereof, that bind the product of a human analogue of a GOI, e.g., an hGOI peptide or protein. Preferably, the antibodies, or portions thereof, are isolated antibodies. Preferably, the antibodies, or portions thereof, are neutralizing antibodies. In one embodiment, the antibodies, or portions thereof, are mAbs. In a preferred embodiment, the mAbs, or portions thereof, contain human heavy or light chains. In an even more preferred embodiment, the mAbs, or portions thereof, contain human heavy and light chains.

In a preferred embodiment, the non human transgenic animal of the invention is immunized with the antigen after treatment with lethal total body irradiation, followed by radioprotection with bone marrow cells of a severe combined immunodeficiency (SCID) mouse, followed by engraftment with functional human lymphocytes. This type of chimera, referred to as the Trimera system, has been used to produce human monoclonal antibodies by immunization of the mice with an antigen of interest followed by preparation of monoclonal antibodies using standard hybridoma technology. For further description of these mice and their use in antibody generation, see for example Eren, R. et al. (1998) *Immunology* 93:154-161; Reisner, Y and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

B-cells from a transgenic host producing immunoglobulin molecules or immunoglobulin molecule analogues may be used to prepare monoclonal antibodies by standard techniques, such as the hybridoma technique originally described by Kohler and Milstein (1975, *Nature* 256:495-497) (see also, Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:26975). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes or lymph node cells or peripheral blood lymphocytes) from a mammal immunized with a specific immunogen as described below, and the culture supernatants of the resulting hybridoma cells are screened to identify a hybridoma producing a monoclonal antibody with specificity for the product of the gene of interest. Any of the many well known protocols used for fusing lymphocytes and immortalized cell lines can be applied for the purpose of generating dual specificity monoclonal antibodies (see, e.g., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled artisan will appreciate that there are many variations of such methods, which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing monoclonal antibodies that specifically recognize the product of the gene of interest are identified by screening the hybridoma culture supernatants for such antibodies, e.g., using a standard ELISA assay, to select those antibodies that specifically can bind the gene product. These immortalized cells may then be grown in continuous culture or introduced into the peritoneum of a compatible host for production of ascites.

The subject invention provides for the production of polyclonal human antisera or human monoclonal antibodies or antibody analogues. A standard in vivo approach to preparing antibodies is by immunizing an appropriate animal subject with an antigen to thereby expose the in vivo antibody repertoire to the antigen, followed by recovery of an antibody or antibodies of interest from the animal. An appropriate immunogenic preparation can contain, for example, a chemically synthesized or recombinantly expressed antigen. The preparation can further include an adjuvant, such as Freund's complete or incomplete adjuvant, or similar immunostimulatory compound. Moreover, when used to raise antibodies, in particular by in vivo immunization, the antigen is used alone, or more preferably is used as a conjugate with a carrier protein. Such an approach for enhancing antibody responses is well known in the art. Examples of suitable carrier proteins to which a dual specificity antigen can be conjugated include keyhole limpet haemocyanin (KLH) and albumin. Where the mammalian host has been immunized with an immunogen, the resulting human antibodies may be isolated from other proteins by using an affinity column, having an Fc binding moiety, such as protein A, or the like.

Antibodies of the invention include dual specificity antibodies. The term "dual specificity antibody," as used herein, is intended to include antibodies that specifically recognize even more than two different but related antigens, such as antibodies that recognize three, four, five or more structurally related but distinct antigens. Furthermore, the term "different but structurally related antigens" is intended to include antigens (e.g., proteins) whose overall structures are related as well as antigens (e.g., proteins) which share one or more structurally-related regions but that are otherwise unrelated. Thus, "different but structurally related" antigens could be, for example, two proteins that are members of the same protein family having a common overall structure or could be, for example, two proteins whose overall structure is dissimilar (unrelated) but that each contain a structurally-related domain. Any of the many well known protocols used for fusing lymphocytes and immortalized cell lines can be applied for the purpose of generating dual specificity monoclonal antibodies (see, e.g., U.S. Pat. No. 5,939,598, PCT Publication No. WO 96/33735, PCT Publication No. WO 96/34096, PCT Publication WO 98/24893 and PCT Publication WO 99/53049 to Abgenix Inc., and U.S. Pat. Nos. 5,897, 861, 6,071,517, and 6,096,311 to Medarex, Inc. See also Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra).

The term "antigen-binding portion" of an antibody (or simply "antibody portion"), as used herein, refers to one or more fragments of an antibody that retain the ability to specifically bind to an antigen (e.g., a human analogue of a GOI product (e.g., an hGOI peptide or protein)). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and*

Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "neutralizing antibody", as used herein (or an "antibody that neutralized an hGOI product activity"), is intended to refer to an antibody whose binding to an hGOI product results in inhibition of the biological activity of an hGOI product. This inhibition of the biological activity of an hGOI product can be assessed by measuring one or more indicators of an hGOI product biological activity. These indicators of an hGOI product biological activity can be assessed by one or more of several standard in vitro or in vivo assays known in the art.

An "isolated dual specificity antibody", as used herein, is intended to refer to a dual specificity antibody that is substantially free of other antibodies having different antigenic specificities (e.g., an isolated antibody that specifically binds two different but structurally related antigens, or structurally-related regions of otherwise unrelated antigens, but that is substantially free of antibodies that specifically bind other unrelated antigens). Moreover, an isolated dual specificity antibody may be substantially free of other cellular material and/or chemicals.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

In one embodiment, the invention pertains to an isolated antibody, or an antigen-binding portion thereof, that binds an epitope of an hGOI product. Preferably, the antibody is a neutralizing antibody. Preferably, the antibody is a monoclonal and/or a human antibody.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$K_{off}$", as used herein, is intended to refer to the off rate constant for dissociation of an antibody from the antibody/antigen complex. The term "$K_d$", as used herein, is intended to refer to the dissociation constant of a particular antibody-antigen interaction.

In other embodiments, the isolated antibody, or antigen-binding portion thereof, binds to an epitope of an hGOI product, wherein the antibody, or antigen-binding portion thereof, dissociates from an hGOI product with a $k_{off}$ rate constant of 0.1 s$^{-1}$ or less, as determined by surface plasmon resonance, or which inhibits an hGOI product activity with an IC$_{50}$ of 1×10$^{-6}$M or less. Alternatively, the antibody, or an antigen-binding portion thereof, may dissociate from an hGOI product with a $k_{off}$ rate constant of 1×10$^{-2}$ s$^{-1}$ or less, as determined by surface plasmon resonance, or may inhibit an hGOI activity with an IC$_{50}$ of 1×10$^{-7}$M or less. Alternatively, the antibody, or an antigen-binding portion thereof, may dissociate from an hGOI with a $k_{off}$ rate constant of 1×10$^{-3}$ s$^{-1}$ or less, as determined by surface plasmon resonance, or may inhibit an hGOI product activity with an IC$_{50}$ of 1×10$^{-8}$M or less. Alternatively, the antibody, or an antigen-binding portion thereof, may dissociate from an hGOI product with a $k_{off}$ rate constant of 1×10$^{-4}$ s$^{-1}$ or less, as determined by surface plasmon resonance, or may inhibit an hGOI activity with an IC$_{50}$ of 1×10$^{-9}$M or less. Alternatively, the antibody, or an antigen-binding portion thereof, may dissociate from an hGOI product with a $k_{off}$ rate constant of 1×10$^{-5}$ s$^{-1}$ or less, as determined by surface plasmon resonance, or may inhibit an hGOI product activity with an IC$_{50}$ of 1×10$^{-10}$M or less. Alternatively, the antibody, or an antigen-binding portion thereof, may dissociate from an hGOI product with a $k_{off}$ rate constant of 1×10$^{-6}$ s$^{-1}$ or less, as determined by surface plasmon resonance, or may inhibit a human analogue of a human analogue of an hGOI product activity with an IC$_{50}$ of 1×10$^{11}$M or less.

Therapeutic Uses

The antibodies and antibody portions of the invention preferably are capable of neutralizing an hGOI product activity both in vitro and in vivo. Accordingly, such antibodies and antibody portions of the invention can be used to inhibit an hGOI product activity, e.g., in a cell culture containing an hGOI product, in human subjects or in other mammalian subjects having an hGOI product with which an antibody of the invention cross-reacts. In one embodiment, the invention provides a method for inhibiting an hGOI product activity comprising contacting an hGOI product with an antibody or antibody portion of the invention such that an hGOI product activity is inhibited. For example, in a cell culture containing, or suspected of containing an hGOI product, an antibody or antibody portion of the invention can be added to the culture medium to inhibit an hGOI product activity in the culture.

In another embodiment, the invention provides a method for inhibiting an hGOI product activity in a subject suffering from a disorder in which an hGOI product activity is detrimental. The invention provides methods for inhibiting an hGOI product activity in a subject suffering from such a disorder, which method comprises administering to the subject an antibody or antibody portion of the invention such that an hGOI product activity in the subject is inhibited. Preferably, the subject is a human subject. Alternatively, the subject can be a mammal expressing an hGOI product with which an antibody of the invention cross-reacts. Still further the subject can be a mammal into which has been introduced an hGOI product (e.g., by administration of an hGOI product or by expression of an hGOI product transgene). An antibody of the invention can be administered to a human subject for therapeutic purposes. Moreover, an antibody of the invention can be administered to a non-human mammal expressing an hGOI product with which the antibody cross-reacts for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which an hGOI product activity is detrimental" is intended to include diseases and other disorders in which the presence of an hGOI product in a subject suffering from the disorder has been shown to be or is suspected of being either responsible for the pathophysiology of the disorder or a factor that contributes to a worsening of the disorder. Accordingly, a disorder in which an activity is detrimental is a disorder in which inhibition of an hGOI product activity is expected to alleviate the symptoms and/or progression of the disorder. Such disorders may be evidenced, for example, by an increase in the concentration of an hGOI product in a biological sample of a subject suffering from the disorder (e.g., an increase in the concentration of an hGOI product in a tissue, serum, plasma, synovial fluid, etc. of the subject), which can be detected, for example, using an anti-hGOI product antibody as described above.

Non-limiting examples of disorders that can be treated with the antibodies of the invention include those disorders discussed in the following section pertaining to pharmaceutical compositions of the antibodies of the invention.

Pharmaceutical Compositions

The invention also provides pharmaceutical compositions an antibody, or antigen-binding portion thereof, of the invention and a pharmaceutically acceptable carrier. In one embodiment, the pharmaceutical composition further comprises at least one additional therapeutic agent for treating a disorder in which an hGOI product activity is detrimental.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is co-formulated with and/or co-administered with one or more additional therapeutic agents that are useful for treating disorders in which an hGOI product activity is detrimental. For example, an anti-hGOI product antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In one embodiment, antibodies or antibody portions of the invention are used to treat pathologies associated with a variety of diseases associated with viral, bacterial, and fungal infections. Such pathologies include, but are not limited to, respiratory infections (e.g., common cold, rhinitis, pharyngitis), croup, bronchiolitis, pneumonitis, rash (e.g., maculopapular, vesicular, hemorrhagic), meningitis, paralysis, encephalitis, conjunctivitis, keratitis, blepharitis, sensorineural hearing loss, parotitis, myocarditis, pericarditis, myositis, myalgia, genital lesions, orchitis, epididymitis, hemorrhagic cystitis, enteritis, hepatitis, teratogenic effects, abortion, stillbirth, fever, sepsis, necrosis, lockjaw, fever, chills, night sweats, anorexia, weight loss, malaise, and skin lesions.

In still another embodiment, antibodies or antibody portions of the invention are used to treat pathology associated with a variety of diseases involving immune and inflammatory elements. Such diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat humans suffering from autoimmune diseases, in particular those associated with inflammation, including, rheumatoid spondylitis, allergy, autoimmune diabetes, and autoimmune uveitis.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition e.g., an agent which effects the viscosity of the composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

III. Methods of Generating Anti-hGOI Product Antibodies

The anti-hGOI product antibodies of the invention are made using any one of a variety of techniques known in the art for preparing antibodies and using antigens comprising an hGOI peptide epitope.

In general, the methods of the invention for making an antibody that binds an hGOI product involve:

exposing an antibody repertoire to an antigen comprising an epitope of an hGOI product; and selecting from the antibody repertoire an antibody that binds the epitope of an hGOI product.

In one embodiment, the antibody repertoire is an in vivo repertoire in an animal which does not functionally express the product of the endogenous GOI, and the method comprises immunizing the animal with the antigen comprising the epitope of an hGOI product. In another embodiment, the antibody repertoire is a recombinant antibody library and the method comprising screening the library with the antigen comprising the epitope of an hGOI peptide. Preferably, the library is a human antibody library.

Methods for immunizing an animal with an antigen to thereby raise specific antibodies to the antigen are well known in the art. An hGOI antigen comprising an epitope of an hGOI product can be administered to an animal to elicit polyclonal antibodies and specific antibodies that bind the epitope can be isolated by selecting from the polyclonal antibodies those antibodies that bind to the epitope (e.g., by passing the polyclonal antisera over a column that comprises a peptide of an hGOI product). The antigen used to elicit the polyclonal antibodies can be intact (i.e., full-length) hGOI product or can be a portion of an hGOI product that includes an epitope of interest. Furthermore, monoclonal antibodies to the epitope can be made from the aforementioned animals using standard hybridoma technology and selection for those hybridomas secreting an antibody that specifically binds the epitope of interest, e.g., by screening the hybridomas with a peptide comprising amino acids of an hGOI product and selecting for antibodies that bind specifically to the peptide.

Recombinant antibody libraries also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, and PCT Publication No. WO 97/29131, the contents of each of which are incorporated herein by reference.

The recombinant antibody library may be from a subject immunized with an hGOI product, or a portion of an hGOI product. Alternatively, the recombinant antibody library may be from a naïve subject, i.e., one who has not been immunized with an hGOI product, such as a human antibody library from a human subject who has not been immunized with an hGOI product. Antibodies of the invention are selected by screening the recombinant antibody library with an epitope of an hGOI product to thereby select those antibodies that recognize this epitope. Methods for conducting such screening and selection are well known in the art, such as described in the references in the preceding paragraph. To select antibodies of the invention having particular binding affinities for an hGOI product, such as those that dissociate from an hGOI product with a particular $k_{off}$ rate constant, the art-known method of surface plasmon resonance can be used to select antibodies having the desired $k_{off}$ rate constant. To select antibodies of the invention having a particular neutralizing activity for an hGOI product, such as those with a particular an $IC_{50}$, standard methods known in the art for assessing the inhibition of an hGOI product activity may be used.

IV. Uses of Anti-hGOI Antibodies

Given their ability to bind to an hGOI product, the anti-hGOI antibodies, or portions thereof, of the invention can be used to detect an hGOI product (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting an hGOI product in a biological sample comprising contacting a biological sample with an antibody, or antibody portion, of the invention and detecting either the antibody (or antibody portion) bound to an hGOI product or unbound antibody (or antibody portion), to thereby detect an hGOI product in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Alternative to labeling the antibody, an hGOI product can be assayed in biological samples by a competition immunoassay utilizing hGOI product standards labeled with a detectable substance and an unlabeled anti-hGOI antibody. In this assay, the biological sample, the labeled hGOI product standards, and the anti-hGOI antibody are combined and the amount of labeled hGOI product standard bound to the unlabeled antibody is determined. The amount of hGOI product in the biological sample is inversely proportional to the amount of labeled hGOI product standard bound to the anti-hGOI antibody. Moreover, the tissue detected can be tissue located in vivo in a subject, e.g., tissue visualized by in vivo imaging of the tissue (e.g., using a labeled antibody)

In another embodiment, the hGOI-product antibodies of the invention can be used for diagnostic purposes (e.g., for diagnosing GOI-mediated diseases or disorders). In one embodiment, an antibody of the invention is used in a diagnostic assay in vitro, such as in a laboratory test to detect the antigen(s) of interest or in a point of care test to detect the antigen(s) of interest. Examples of well-established in vitro assays utilizing antibodies include ELISAs, RIAs, Western blots and the like. In another embodiment, an antibody of the invention is used in a diagnostic assay in vivo, such as an in vivo imaging test. For example, the antibody can be labeled with a detectable substance capable of being detected in vivo, the labeled antibody can be administered to a subject, and the labeled antibody can be detected in vivo, thereby allowing for in vivo imaging.

Imaging techniques suitable for detecting GOI-mediated diseases or disorders include biophysical assays such as: circular dichroism, electron microscopy, and fluorescence, as well as immunological and biochemical assays such as in situ hybridization, immunohistology, immunostaining, immunoprecipitation, Western blotting, ELISA assays and the like. Such techniques are commonly used and known to those of skill in the art (Harlow, E. and Lane, D. *Antibodies: A Laboratory Manual*, Cold Spring Harbor Laboratory Press, Cold Spring Harbor, N.Y., 1988; Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989; and Ausubel et al. *Current Protocols in Molecular Biology*, John Wiley & Sons, Inc. (1995)).

The hGOI-product antibodies of the invention can be used to produce binding molecules specific for the hGOI-product. Methods of differential display utilizing phage, yeast or viral systems are known in the art and may be used to screen for binding molecules and/or binding partners of the immunoglobulins of the invention (Liang et al. (1994) *Nucleic Acids Res.* 22:5763-5764; Ikeda et al. (1997) *Science* 276:1564-1566; Taylor et al. (1996) *J. Biol. Chem.* 271:20399-20405). For example, a library of organisms which display immunoglobulins at their cell surfaces can be used to produce such binding molecules. The organisms each contain a nucleic acid with sequence derived from any of the transgenic animals, unimmunized with the hGOI antigen, as described herein. Because the animal is unimmunized, it does not express immunoglobulin molecules specific for the hGOI antigen found in the sera. The organisms making up the library encode a polypeptide chain which is a component part of the immunoglobulin displayed at the surface of that organism. Immunoglobulins are then selected by their ability to bind the hGOI antigen.

In another embodiment, the hGOI-product antibodies of the invention can be used to synthesize DNA libraries capable of encoding one or more families of antigen-combining proteins. Various methods of generating DNA libraries are known in the art (Gubler et al. (1983) *Gene* 25:263-269; Hagen et al. (1988) *BioTechniques* 6:340-345). For example, DNA encoding a diverse set of antigen-combining proteins can be isolated from one or more tissue sample(s) from one or more of the non-human transgenic animal(s) described herein. The DNA can then be combined with sequence specific primers, which are oligonucleotides having sequence similarity with conserved regions of the DNA. Sequence specific gene amplification can then be performed by inserting the amplified DNA into the variable region of said heavy chain gene encoded within a framework antibody expression vector. The expression vector is then mixed with a vector comprising an immunoglobulin light chain gene, and both vectors are transfected into a cell, thus creating a library of cells producing both light chain immunoglobulins and heavy chain immunoglobulins.

The contents of all cited references, including literature references, issued patents, and published patent applications, as cited throughout this application are hereby expressly incorporated by reference.

This invention is further illustrated by the following examples which should not be construed as limiting.

EXAMPLES

Materials and Methods

In general, the practice of the present invention employs, unless otherwise indicated, conventional techniques of animal husbandry, chemistry, molecular biology, recombinant DNA technology, PCR technology, immunology, microbiology, or cell culture, which are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *PCR Handbook Current Protocols in Nucleic Acid Chemistry*, Beaucage, Ed. John Wiley & Sons (1999); *Antibodies: A Laboratory Manual*, Harlow et al., C.S.H.L. Press, Pub. (1999); *Bergey's Manual of Determinative Bacteriol-*

*ogy*, Kreig et al., Williams and Wilkins (1984), and *Current Protocols in Molecular Biology*, eds. Ausubel et al., Wiley Interscience (1998).

For additional techniques for generating knockout and transgenic mice see, e.g., von Melchner et al. (1992) *Genes Dev.* 1992 6(6):919-27; Gossler et al. (1989) *Science* 244 (4903):463-5; Deng et al. (1995) *Transgenic Res.* 4(4):264-9; Friedrich et al. (1991) *Genes Dev.* 5(9):1513-23; Soriano et al. (1991) *J. Virol.* 65(5):2314-9; Skames et al. (1992) *Genes Dev.* 6(6):903-18; Joyner et al. (1989) *Nature* 338(6211):153-6; Capecchi (1989) *Science* 244(4910):1288-92; Sauer (1998) *Meth. Enz.* 14(4):381-92; and Rossi et al. (1998) *Curr. Opin. Biotechnol.* 9(5):451-6.

Unless otherwise stated, the following materials and methods were used in the examples that follow.

Example 1

Methods for Generating Endogenous Ig Knockout Mice which Express Human Ig Molecules Different approaches can be taken to generate knockout (KO) mice with human Ig transgenes. Some examples and their uses are listed below.

A. Inter-Breeding of Knockout Mice with the Transgenic Mice

This method is used when the gene of interest and the human Ig transgenes are on separate chromosomes. Mice with a knocked out IgG gene are bred with mice expressing the transgenes for human IgG H and L chains. First generation progeny (F1) which are heterozygous for the human IgG gene are then bred, generating second generation progeny (F2) which include mice homozygous for the H-chain or the L-chain, each at a frequency of $1/16$.

Step 1:
(−/− murine IgG KO mice)×(+/+ mice human H and L kappa chains IgG)
F1=(−/+, mu/hu IgG)×(−/+, mu/hu IgG)
F2=−/−, hu H-chain/hu H-chain Ig at a frequency of $1/16$(F2H: KO/huHIgG)
F2=−/−, hu L-chain/hu L-chain Ig at a frequency of $1/16$(F2L: Ko/huLIgG)

F2H mice have murine L-chains and generate chimeric mAbs with human heavy chain and murine light chains. The human heavy chains from such mAbs are used in vitro to select for the complimentary human Light chains using the phage display technology. Similarly, chimeric mAbs from F2L mice are used in vitro to select complimentary human heavy chains using phage display technology.

The second step of breeding generates mice with a murine IgG knockout that express human H-chain and human L-chain IgG transgenes. F2 mice homozygous for an H-chain or a L-chain are bred with F2 mice homozygous for a L-chain or an H-chain, respectively. Third generation progeny (F3) which are homozygous for the human IgG H-chain and L-chain genes are generated at a frequency of $1/16$. In step three, the homozygous human H-chain and human L-chain IgG transgenic mice are bred with one another to generate fourth generation progeny (F4) which all express human H-chain and human L-chain IgG transgenes. Such mice generate fully human mAbs.

Step 2:
F2H×F2L
F3=−/−, hu H-chain, hu L-chain Ig at a frequency of $1/16$
Step 3:
F3×F3
F4=−/−, hu H-chain, hu L-chain at a frequency of 100%

B. Directly Deleting a Gene of Interest in a Transgenic Mouse

The target is also inactivated or knocked-out through means such as homologous recombination, random insertion, chemical mutagenesis, or expression of antisense RNA. In addition, the target gene is inactivated or knocked-out conditionally by combining the above approach with the cre/Lox system or with inducible gene expression systems.

These methods would be more applicable when the gene of interest and the human Ig transgenes are on the same chromosome. Such KO-Tg mice would not be tolerant to the protein of interest and upon immunization generate high affinity fully human antibodies against all regions of the protein of interest.

Example 2

Methods for Generating Mouse-Anti-Mouse IL-18 mAbs Using IL-18 Knockout Mice

Immunization of IL-18 knockout mice with mouse IL-18 was conducted as follows. An emulsion of murine IL-18 (125 ug/ml) was prepared in Complete Freund's Adjuvant (CFA) and Incomplete Freund's Adjuvant (ICFA). On day 0, mice were immunized with 150 ul/mouse of the CFA-emulsion into 3 sites (50 ul into each footpad and 50 ul into base of tail ID=approx. 18 ug/mouse). On days 21 and 35, the mice were boosted with 100 ul ID at the base of tail with ICFA-emulsion containing murine IL-18 (approximately 12 ug/mouse).

On day 37, serum was collected from control (non-immunized/boosted) C57BL/6J mice and the 5 immunized/boosted IL-18 knockout mice to determine titers of anti-murine IL-18 antibodies. On day 85, the animals were boosted with 10 ug IL-18 per mouse intravenously in phosphate buffered saline in a volume of 100 ul. On day 89, animals were terminally bled for serum and spleens and lymph nodes were harvested for fusions with SP2/O myeloma cells. Fusions were carried out by routine methods known to those of skill in the art.

Two weeks after the fusions, hybridomas making monoclonal antibodies to mouse IL-18 were selected using an ELISA-based assay. The hybridomas were then tested for their ability to neutralize mouse IL-18 functions in an mouse splenocyte-based assay. The positive hybridomas were selected, sub-cloned and expanded.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A transgenic mouse having an ablated immune system, whose genome comprises:
(a) at least one inactivated endogenous heavy or light chain immunoglobulin gene;
(b) an alteration in a second endogenous gene such that the gene product of the second endogenous gene is not produced;
wherein said transgenic mouse further comprises engrafted mouse bone marrow cells expressing at least one human immunoglobulin gene, obtained from a mouse transgenic for at least one human immunoglobulin gene;

and whereupon exposure to the second gene product, the transgenic mouse expresses a functional human immunoglobulin, or portion thereof, that binds the second gene product.

2. The transgenic mouse of claim 1, wherein the endogenous immunoglobulin locus comprises a gene encoding a protein selected from the group consisting of an endogenous heavy chain, an endogenous light chain, and both an endogenous heavy chain and an endogenous light chain.

3. The transgenic mouse of claim 1, wherein the human immunoglobulin is selected from the group consisting of a human heavy chain, a human light chain, and both a human heavy chain and a human light chain.

4. A transgenic mouse having an ablated immune system, whose genome comprises:
(a) at least one of an inactivated endogenous heavy chain and light chain immunoglobulin gene;
(b) an alteration in a second endogenous gene such that the gene product of the second endogenous gene is not produced;
wherein said transgenic mouse further comprises engrafted mouse bone marrow cells expressing at least one human immunoglobulin gene, obtained from a mouse transgenic for at least one human immunoglobulin gene;
and whereupon exposure to a human homologue of the second gene product, the transgenic mouse expresses a functional human immunoglobulin, or portion thereof, that binds the human homologue of the gene product.

5. The transgenic mouse of any one of claims 1 and 4, wherein the human immunoglobulin is IgG, IgM or IgA.

6. The transgenic mouse of any one of claims 1 and 4, wherein the alteration in the second endogenous gene is a naturally-occurring or a genetically engineered disruption or excision.

7. The transgenic mouse of claim 6, wherein the gene product is selected from the group consisting of an IFN, a TNF, an Interleukin, a cytokine, IP-10, PF4, a GRO, 9E3, EMAP-II, a CSF, an FGF, and a PDGF.

8. The transgenic mouse of claim 7, wherein the interleukin is selected from the group consisting of IL-1$\alpha$, IL-1$\beta$, IL-12, and IL-18.

9. The transgenic mouse of any one of claims 1 and 4, wherein the gene product of the second endogenous gene is highly conserved structurally and functionally between human and mouse, and wherein the immunoglobulin is raised against an epitope of the gene product that is conserved.

10. Progeny obtained from the transgenic mouse of any one of claims 1, 4, and 9.

* * * * *